(12) United States Patent
Kim et al.

(10) Patent No.: US 12,091,448 B2
(45) Date of Patent: Sep. 17, 2024

(54) BINDING MOLECULE ABLE TO NEUTRALIZE PROX1 PROTEIN

(71) Applicant: Korea Advanced Institute of Science and Technology, Daejeon (KR)

(72) Inventors: Jin Woo Kim, Daejeon (KR); Eun Jung Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 18/089,393

(22) Filed: Dec. 27, 2022

(65) Prior Publication Data

US 2023/0331829 A1    Oct. 19, 2023

(30) Foreign Application Priority Data

Dec. 29, 2021    (KR) .................. 10-2021-0190878

(51) Int. Cl.
*C07K 16/18*    (2006.01)
*C12N 15/86*    (2006.01)

(52) U.S. Cl.
CPC .............. *C07K 16/18* (2013.01); *C12N 15/86* (2013.01); *C07K 2317/24* (2013.01); *C07K 2317/565* (2013.01); *C07K 2317/622* (2013.01); *C12N 2750/14143* (2013.01)

(58) Field of Classification Search
CPC ............... C07K 16/18; C07K 2317/24; C07K 2317/565; C07K 2317/622; C07K 16/2863; C07K 2317/56; C07K 2317/76; C07K 2319/20; C12N 15/86; C12N 2750/14143; A61K 39/3955; A61K 2039/505; A61P 27/02
See application file for complete search history.

(56) References Cited

U.S. PATENT DOCUMENTS

| | | |
|---|---|---|
| 2003/0224516 A1 | 12/2003 | Dobie |
| 2005/0271636 A1 | 12/2005 | Oliver et al. |
| 2007/0048313 A1 | 3/2007 | Duncan et al. |
| 2021/0228741 A1 | 7/2021 | Reh et al. |
| 2023/0029377 A1 | 1/2023 | Kim et al. |

FOREIGN PATENT DOCUMENTS

| | | |
|---|---|---|
| EP | 4173641 A1 | 5/2023 |
| WO | 2021261965 A1 | 12/2021 |

OTHER PUBLICATIONS

Almagro et al. Humanization of antibodies. Front Biosci. 13:1619-33, 2008. (Year: 2008).*
Gershoni et al. Epitope mapping: the first step in developing epitope-based vaccines. Biodrugs. 21 (3): 145-156, 2007. (Year: 2007).*
Blythe et al. Benchmarking B cell epitope prediction: Underperformance of existing methods. Protein Science. 14:246-248, 2005. (Year: 2005).*
Schreiber et al. 3D-Epitope-Explorer (3DEX): Localization of conformational epitopes within three-dimensional structures of proteins. Journal of Computational Chemistry. 26(9) 879-887, 2005. (Year: 2005).*
European Search Report (EESR) for corresponding 22217161.3, completed May 4, 2023, pp. 1-8.
Zhu Lizhe et al., "PROXI promotes breast 1-13 cancer invasion and metastasis through WNT/[beta]-catenin pathway via interacting with hnRNPK", International Journal of Biological Sciences, vol. 18, No. 5, Feb. 28, 2022 (Feb. 28, 2022), pp. 2032-2046, XP93044047, ISSN: 1449-2288, DOI: 10.7150/ijbs.68960, Retrieved from the Internet: URL:https://www.ijbs.com/v18p2032.pdf> *abstract*.
Michael A. Dyer et al., "Prox1 function controls progenitor cell proliferation and horizontal cell genesis in the mammalian retina" 2003 Nature Publishing Group, Apr. 14, 2003; doi:10.1038/ng1144, pp. 1-6.
Elena Cid et al., "Prox1 expression in rod precursors and Müller cells" Experimental Eye Research 90, (2010), pp. 267-276.
Korea Advanced Institute of Science and Technology; "Binding Molecule Able To Neutralize PROX1 Protein"; Korean Application No.: Application No. 10-2021-0190878; Korean Office Action dated Jun. 5, 2024; 6 pgs.

* cited by examiner

*Primary Examiner* — Brad Duffy
*Assistant Examiner* — Amber K Faust
(74) *Attorney, Agent, or Firm* — Tarolli, Sundheim, Covell & Tummino LLP

(57) ABSTRACT

The present disclosure relates to a PROX1 (Prospero homeobox protein 1) protein binding molecule. More specifically, the binding molecule of the present disclosure relates to a binding molecule having excellent binding ability to the PROX1 protein and having an excellent neutralizing effect on the PROX1 protein, and it is very useful for diagnosis, prevention or treatment of retinal neurodegenerative diseases.

5 Claims, 12 Drawing Sheets

Specification includes a Sequence Listing.

[FIG. 1]

[FIG. 3B]
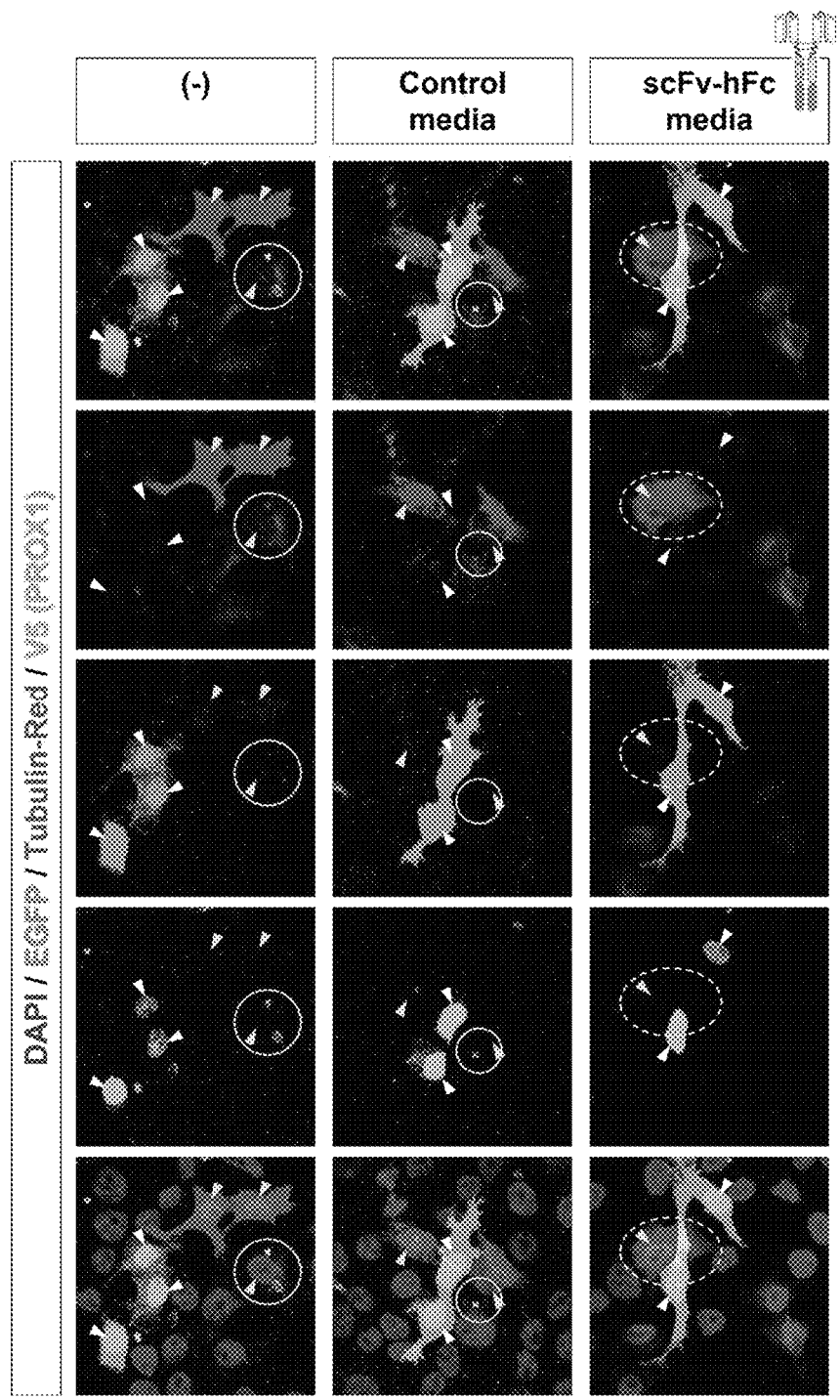

[FIG. 4A]
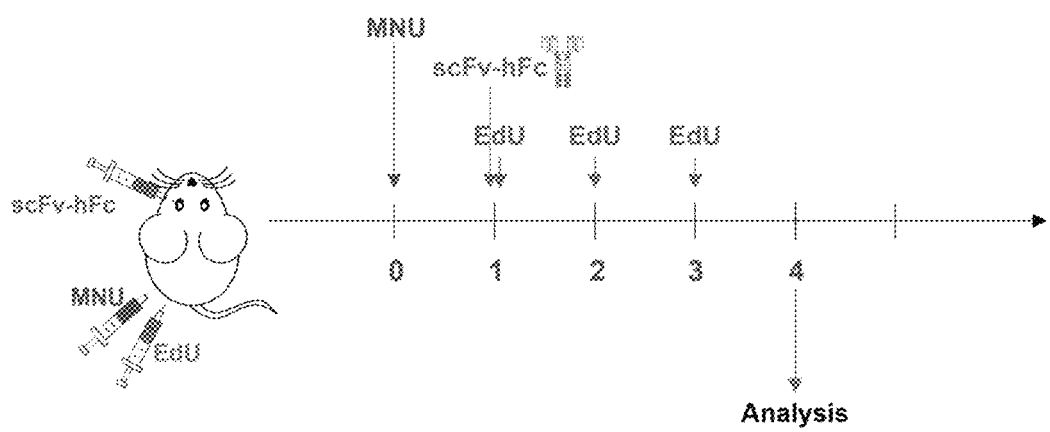

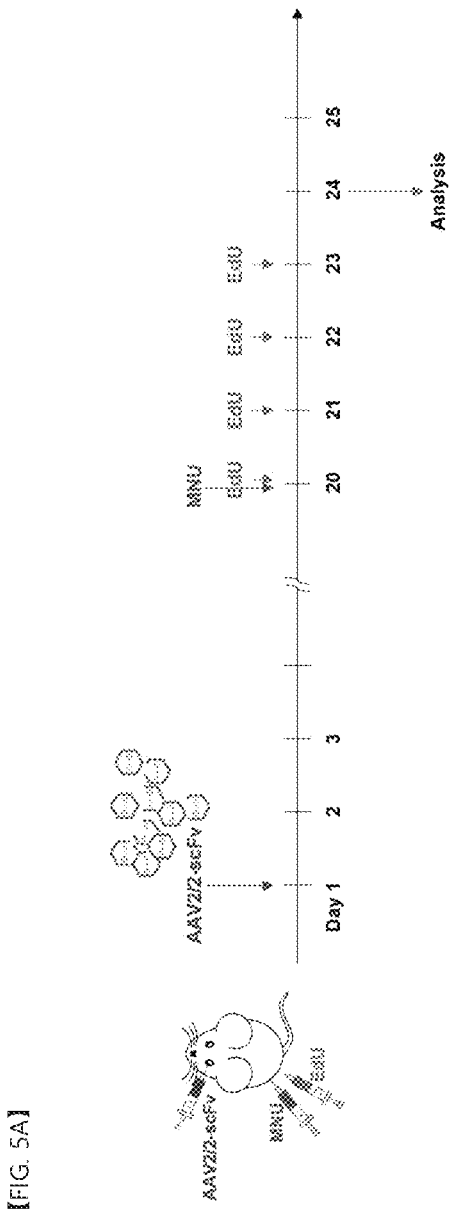

[FIG. 5B]
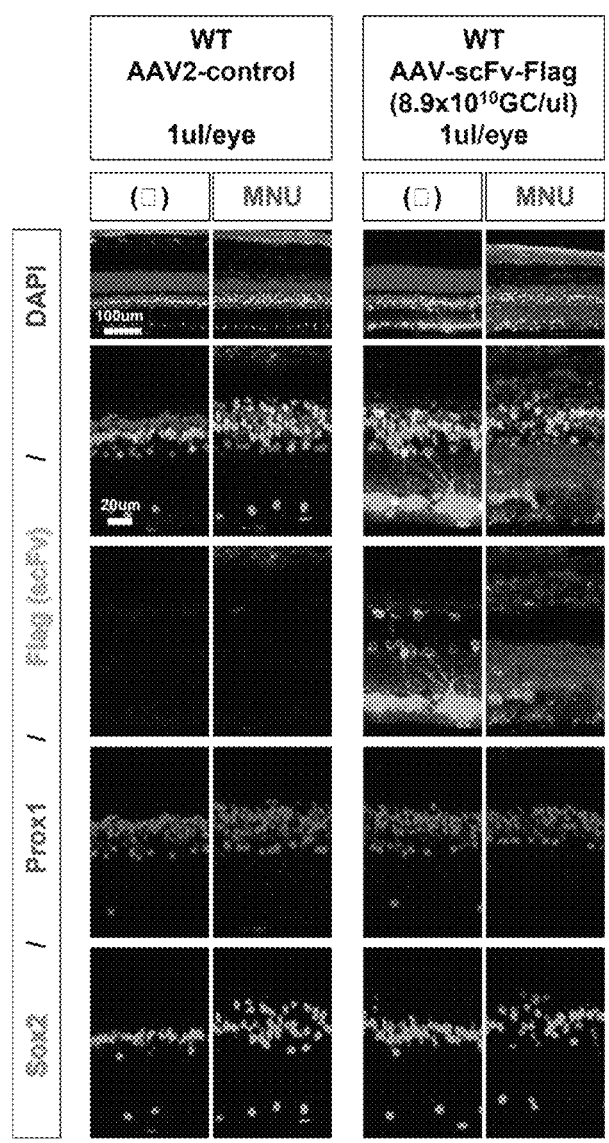

[FIG. 7]

scFv-His sequence (clone#1A11)

>DNA sequence (SEQ No. 2)

AACCTGAGATTAAATGAGAAGACAGCTATCGCGATTGCAGTGGCACTGGCTGGTTTCGCTACCGTGGCCCAGGCGGCCCT
GACTCAGCCGTCCTCGGTGTCAGCAAACCTAGGAGAAACCGTCGAGATCACCTGCTCCGGGGGTAGTGGCAGCTATGGCT
GGTATCAGCAGAAGTCACCTGGCAGTGCCCCTGTCACTCTGATCTATGACAACGCCAACAGACCCTCGAACATCCCTTCAC
GATTCTCCGGTTCCAAATCCGGCTCCACGGGCACATTAACCATCACTGGGGTCCGAGCCGAGGATGAGGCTGTCTATTACT
GTGGGAATGTAGACAGCAGCACTTATGTTGGTATGTTTGGGGCCGGGACAACCCTGACCGTCCTAGGTCAGTCCTCTAGAT
CTTCCGGCGGTGGTGGCAGCTCCGGTGGTGGCGGTTCCGCCGTGACGTTGGACGAGTCCGGGGCGGCCTCCAGACGCC
CGGAGGAGGGCTCAGCCTCGTCTGCAAGGCCTCCGGGTTCACCTTCAGCAGTTATGCCATGAACTGGGTGCGACAGGCG
CCCGGCAAGGGGCTGGAGTGGGTCGCTGCTATTGATGATGATGGTAGTTACACAGGCTACGGGTCGGCGGTGAAGGGCC
GTGCCACCATCTCGAGGGACAACGGGCAGAGCACAGTGAGGCTGCAGCTGAACAACCTCAGGGCTGAGGACACCGCCA
TCTACTACTGCGCCAAAGCTGCTGGTAGTGGTTACTGTTATCGTGGTGCTAATAGTAGTTATACTTGTGGTACTTATAACGCTG
GTGACATCGACGCATGGGGCCACGGGACCGAAGTCATCGTCTCCTCCACTAGTGGCCAGGCCGGCCAGCACCATCACCAT
CACCATGGCGCATACCCGTACGACGTTCCGGACTACGCTTCTTAGGAGGGTGGTGGCTCTGAGGGTGGCGGTTCTGAGGG
TGGCGGCTCTGAGGGAGGCGGTTCCGGTGGTGGCTCTGGTTCCGGTGATTTTGATTATGAAAAGATGGCAAACGCTAATAA
GGGGGCTATGACCGAAAATGCCGATGAAAACGTGCTACAGTCTGACGCTAAAGGCAAACTTGATTCTGTCGCTACTGATTA
CGGTGCTGCTATCGATGGTTTCATTGGTGACGTTTCCGGCCTTGCTAATGGTAATGGTGCTACTGGGGATTTTGCTGGCTCTA
ATTCCCAAATGGCTCAG

>Protein sequence (SEQ No. 1)

LTQPSSVSANLGETVEITCSGGSGSYGWYQQKSPGSAPVTLIYDNANRPSNIPSRFSGSKSGSTGTLTITGVRAEDEAVYYCGN
VDSSTYVGMFGAGTTLTVLGQSSRSSGGGGSSGGGGSAVTLDESGGGLQTPGGGLSLVCKASGFTFSSYAMNWVRQAPGK
GLEWVAAIDDDGSYTGYGSAVKGRATISRDNGQSTVRLQLNNLRAEDTAIYYCAKAAGSGYCYRGANSSYTCGTYNAGDIDA
WGHGTEVIVSSTSGQAGQHHHHHHGAYPYDVPDYAS

[FIG. 8]

scFv-hFc sequence

>DNA sequence (SEQ No. 13)

ATGGAGACAGACACACTCCTGCTATGGGTACTGCTGCTCTTAGCGGCCCAGCCGGCCCTGACTCAGCCGTCCTCGGTGTCA
GCAAACCTAGGAGAAACCGTCGAGATCACCTGCTCCGGGGGTAGTGGCAGCTATGGCTGGTATCAGCAGAAGTCACCTGGG
CAGTGCCCCTGTCACTCTGATCTATGACAACGCCAACAGACCCTCGAACATCCCTTCACGATTCTCCGGTTCCAAATCCGGC
TCCACGGGCACATTAACCATCACTGGGGTCCGAGCCGAGGATGAGGCTGTCTATTACTGTGGGAATGTAGACAGCAGCACT
TATGTTGGTATGTTTGGGGCCGGGACAACCCTGACCGTCCTAGGTCAGTCCTCTAGATCTTCCGGCGGTGGTGGCAGCTCCG
GTGGTGGCGGTTCCGCCGTGACGTTGGACGAGTCCGGGGGCGGCCTCCAGACGCCCGGAGGAGGGCTCAGCCTCGTCTG
CAAGGCCTCCGGGTTCACCTTCAGCAGTTATGCCATGAACTGGGTGCGACAGGCGCCCGGCAAGGGGCTGGAGTGGGTC
GCTGCTATTGATGATGATGGTAGTTACACAGGCTACGGGTCGGCGGTGAAGGGCCGTGCCACCATCTCGAGGGACAACGG
GCAGAGCACAGTGAGGCTGCAGCTGAACAACCTCAGGGCTGAGGACACCGCCATCTACTACTGCGCCAAAGCTGCTGGT
AGTGGTTACTGTTATCGTGGTGCTAATAGTAGTTATACTTGTGGTACTTATAACGCTGGTGACATCGACGCATGGGGCCACGG
GACCGAAGTCATCGTCTCCTCCACTAGTGGCCCGGGAGGCCCCGAGCCCAAATCTTCTGACAAAACTCACACATGCCCACC
GTGCCCAGCACCTGAACTCCTGGGGGGACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGTGTGGTCAGCGTCCTCACCG
TCCTGCACCAGGACTGGCTGAATGGCAAGGAGTACAAGTGCAAGGTGTCCAACAAAGCCCTCCCAGCCCCCATCGAGAA
AACCATCTCCAAAGCCAAAGGGCAGCCCCGAGAACCACAGGTGTACACCCTGCCCCCATCCCGGGATGAGCTGACCAAG
AACCAGGTCAGCCTGACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTATAGCAAGCTCACCGTGGACA
AGAGCAGGTGGCAGCAGGGGAACGTCTTCTCATGCTCCGTGATGCATGAGGCTCTGCACAACCACTACACGCAGAAGAG
CCTCTCCCTGTCTCCGGGTAAATGA

>Protein sequence (SEQ No. 12)

METDTLLLWVLLLAAQPALTQPSSVSANLGETVEITCSGGSGSYGWYQQKSPGSAPVTLIYDNANRPSNIPSRFSGSKSGSTG
TLTITGVRAEDEAVYYCGNVDSSTYVGMFGAGTTLTVLGQSSRSSGGGGSSGGGGSAVTLDESGGGLQTPGGGLSLVCKASGF
TFSSYAMNWVRQAPGKGLEWVAAIDDDGSYTGYGSAVKGRATISRDNGQSTVRLQLNNLRAEDTAIYYCAKAAGSGYCYRG
ANSSYTCGTYNAGDIQAWGHGTEVIVSSTSGPGGPEPKSSDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKLTVDKSRWQQGNVFSCSVM
HEALHNHYTQKSLSLSPGK*

[FIG. 9]

AAV2/2-IL2'SP-anti-PROX1-scFv-Flag

>DNA sequence (SEQ No. 15)
ATGTACAGAATGCAACTCCTGTCTTGTATTGCACTAAGTCTCGCACTTGTCACAAACAGTatgCTGACTCAGCCGTCCTCGGT
GTCAGCAAACCTAGGAGAAACCGTCGAGATCACCTGCTCCGGGGGTAGTGGCAGCTATGGCTGGTATCAGCAGAAGTCAC
CTGGCAGTGCCCCTGTCACTCTGATCTATGACAACGCCAACAGACCCTCGAACATCCCTTCACGATTCTCCGGTTCCAAATC
CGGCTCCACGGGCACATTAACCATCACTGGGGTCCGAGCCGAGGATGAGGCTGTCTATTACTGTGGAATGTAGACAGCA
GCACTTATGTTGGTATGTTTGGGGCCGGGACAACCCTGACCGTCCTAGGTCAGTCCTCTAGATCTTCCGGCGGTGGTGGCA
GCTCCGGTGGTGGCGGTTCCGCCGTGACGTTGGACGAGTCCGGGGGCGGCCTCCAGACGCCCGGAGGAGGGCTCAGCC
TCGTCTGCAAGGCCTCCGGGTTCACCTTCAGCAGTTATGCCATGAACTGGGTGCGACAGGCGCCCGGCAAGGGGCTGGA
GTGGGTCGCTGCTATTGATGATGATGGTAGTTACACAGGCTACGGGTCGGCGGTGAAGGGCCGTGCCACCATCTCGAGGG
ACAACGGGCAGAGCACAGTGAGGCTGCAGCTGAACAACCTCAGGGCTGAGGACACCGCCATCTACTACTGCGCCAAAG
CTGCTGGTAGTGGTTACTGTTATCGTGGTGCTAATAGTAGTTATACTTGTGGTACTTATAACGCTGGTGACATCGACGCATGGG
GCCACGGGACCGAAGTCATCGTCTCCTCCACTAGTGGCCAGGCCGGCCAGatggactacaaagatgatgacgacaaagTAGTAG

>Protein sequence (SEQ No. 14)
MYRMQLLSCIALSLALVTNSMLTQPSSVSANLGETVEITCSGGSGSYGWYQQKSPGSAPVTLIYDNANRPSNIPSRFSGSKSG
STGTLTITGVRAEDEAVYYCGNVDSSTYVGMFGAGTTLTVLGQSSRSSGGGGSGGGGSAVTLDESGGGLQTPGGGLSLVCKA
SGFTFSSYAMNWVRQAPGKGLEWVAAIDDDGSYTGYGSAVKGRATISRDNGQSTVRLQLNNLRAEDTAIYYCAKAAGSGYC
YRGANSSYTCGTYNAGDIDAWGHGTEVIVSSTSGQAGQMDYKDDDDK**

SEQUENCE LISTING

```
Sequence total quantity: 15
SEQ ID NO: 1            moltype = AA   length = 282
FEATURE                 Location/Qualifiers
REGION                  1..282
                        note = anti-PROX1-single chain Fv-His
source                  1..282
                        mol_type = protein
                        organism = synthetic construct
SEQUENCE: 1
LTQPSSVSAN LGETVEITCS GGSGSYGWYQ QKSPGSAPVT LIYDNANRPS NIPSRFSGSK    60
SGSTGTLTIT GVRAEDEAVY YCGNVDSSTY VGMFGAGTTL TVLGQSSRSS GGGGSSGGGG   120
SAVTLDESGG GLQTPGGGLS LVCKASGFTF SSYAMNWVRQ APGKGLEWVA AIDDDGSYTG   180
YGSAVKGRAT ISRDNGQSTV RLQLNNLRAE DTAIYYCAKA AGSGYCYRGA NSSYTCGTYN   240
AGDIDAWGHG TEVIVSSTSG QAGQHHHHHH GAYPYDVPDY AS                      282

SEQ ID NO: 2            moltype = DNA   length = 1224
FEATURE                 Location/Qualifiers
misc_feature            1..1224
                        note = anti-PROX1-single chain Fv-His
source                  1..1224
                        mol_type = other DNA
                        organism = synthetic construct
SEQUENCE: 2
aacctgagat taaatgagaa gacagctatc gcgattgcag tggcactggc tggtttcgct    60
accgtggccc aggcggccct gactcagccg tcctcggtgt cagcaaacct aggagaaacc   120
gtcgagatca cctgctccgg gggtagtggc agctatggct ggtatcagca gaagtcacct   180
ggcagtgccc ctgtcactct gatctatgac aacgccaaca gaccctcgaa catcccttca   240
cgattctccg gttccaaatc cggctccacg ggcacattaa ccatcactgg ggtccgagcc   300
gaggatgagg ctgtctatta ctgtgggaat gtagacagca gcacttatgt tggtatgttt   360
ggggccggga caaccctgac cgtcctaggt cagtcctcta gatcttccgg cggtggtggc   420
agctccggtg gtggcggttc cgccgtgacg ttggacgagt ccggggggcgg cctccagacg   480
cccggaggag ggctcagcct cgtctgcaag gcctccggat tcaccttcag cagttatgcc   540
atgaactggg tgcgacaggc gcccggcaag ggctgagtg gggtcgctgc tattgatgat   600
gatggtagtt acacaggcta cggtcgcg gtgaagggcc gtgccaccat ctcgaggac     660
aacgggcaga gcacagtgag gctgcagctg aacaacctca gggctgagga caccgccatc   720
tactactgcg ccaaagctgc tggtagtggt tactgttatc gtggtgctaa tagtagttat   780
acttgtggta cttataacgc tggtgacatc gacgcatggg gccacgggac cgaagtcatc   840
gtctcctcca ctagtggcca ggccggccag caccatcacc atcaccatgg cgcatacccg   900
tacgacgttc cggactacgc ttcttaggag ggtggtggct ctgagggtgg cggttctgag   960
ggtggcggct ctgagggagg cggttccggt ggtggctctg gttccggtga ttttgattat  1020
gaaaagatgg caaacgctaa taggggggct atgaccgaaa atgccgataa aaacgtgcta  1080
cagtctgacg ctaaaggcaa acttgattct gtcgctactg attacggtgc tgctatcgat  1140
ggtttcattg gtgacgtttc cggccttgct aatggtaatg gtgctactgg gattttgct   1200
ggctctaatt cccaaatggc tcag                                         1224

SEQ ID NO: 3            moltype = AA   length = 103
FEATURE                 Location/Qualifiers
REGION                  1..103
                        note = anti-PROX1-single chain Fv-His light chain
source                  1..103
                        mol_type = protein
                        organism = synthetic construct
SEQUENCE: 3
LTQPSSVSAN LGETVEITCS GGSGSYGWYQ QKSPGSAPVT LIYDNANRPS NIPSRFSGSK    60
SGSTGTLTIT GVRAEDEAVY YCGNVDSSTY VGMFGAGTTL TVL                     103

SEQ ID NO: 4            moltype = AA   length = 138
FEATURE                 Location/Qualifiers
REGION                  1..138
                        note = anti-PROX1-single chain Fv-His heavy chain
source                  1..138
                        mol_type = protein
                        organism = synthetic construct
SEQUENCE: 4
AVTLDESGGG LQTPGGGLSL VCKASGFTFS SYAMNWVRQA PGKGLEWVAA IDDDGSYTGY    60
GSAVKGRATI SRDNGQSTVR LQLNNLRAED TAIYYCAKAA GSGYCYRGAN SSYTCGTYNA   120
GDIDAWGHGT EVIVSSTS                                                 138
```

```
SEQ ID NO: 5            moltype = AA  length = 18
FEATURE                 Location/Qualifiers
REGION                  1..18
                        note = anti-PROX1-single chain Fv-His linker
source                  1..18
                        mol_type = protein
                        organism = synthetic construct
SEQUENCE: 5
GQSSRSSGGG GSSGGGGS                                                       18

SEQ ID NO: 6            moltype = AA  length = 7
FEATURE                 Location/Qualifiers
REGION                  1..7
                        note = anti-PROX1-single chain Fv-His CDR1
source                  1..7
                        mol_type = protein
                        organism = synthetic construct
SEQUENCE: 6
GGSGSYG                                                                    7

SEQ ID NO: 7            moltype = AA  length = 4
FEATURE                 Location/Qualifiers
REGION                  1..4
                        note = anti-PROX1-single chain Fv-His CDR2
source                  1..4
                        mol_type = protein
                        organism = synthetic construct
SEQUENCE: 7
DNAN                                                                       4

SEQ ID NO: 8            moltype = AA  length = 8
FEATURE                 Location/Qualifiers
REGION                  1..8
                        note = anti-PROX1-single chain Fv-His CDR3
source                  1..8
                        mol_type = protein
                        organism = synthetic construct
SEQUENCE: 8
GNVDSSTY                                                                   8

SEQ ID NO: 9            moltype = AA  length = 5
FEATURE                 Location/Qualifiers
REGION                  1..5
                        note = anti-PROX1-single chain Fv-His CDR4
source                  1..5
                        mol_type = protein
                        organism = synthetic construct
SEQUENCE: 9
SYAMN                                                                      5

SEQ ID NO: 10           moltype = AA  length = 10
FEATURE                 Location/Qualifiers
REGION                  1..10
                        note = anti-PROX1-single chain Fv-His CDR5
source                  1..10
                        mol_type = protein
                        organism = synthetic construct
SEQUENCE: 10
IDDDGSYTGY                                                                10

SEQ ID NO: 11           moltype = AA  length = 28
FEATURE                 Location/Qualifiers
REGION                  1..28
                        note = anti-PROX1-single chain Fv-His CDR6
source                  1..28
                        mol_type = protein
                        organism = synthetic construct
SEQUENCE: 11
KAAGSGYCYR GANSSYTCGT YNAGDIDA                                            28

SEQ ID NO: 12           moltype = AA  length = 1545
FEATURE                 Location/Qualifiers
REGION                  1..1545
                        note = anti-PROX1-scFv-hFc
source                  1..1545
                        mol_type = protein
                        organism = synthetic construct
SEQUENCE: 12
```

```
METGLUTHRA SPTHRLEULE ULEUTRPVAL LEULEULEUL EUALAALAGL NPROALALEU   60
THRGLNPROS ERSERVALSE RALAASNLEU GLYGLUTHRV ALGLUILETH RCYSSERGLY  120
GLYSERGLYS ERTYRGLYTR PTYRGLNGLN LYSSERPROG LYSERALAPR QVALTHRLEU  180
ILETYRASPA SNALAASNAR GPROSERASN ILEPROSERA RGPHESERGL YSERLYSSER  240
GLYSERTHRG LYTHRLEUTH RILETHRGLY VALARGALAG LUASPGLUAL AVALTYRTYR  300
CYSGLYASNV ALASPSERSE RTHRTYRVAL GLYMETPHEG LYALAGLYTH RTHRLEUTHR  360
VALLEUGLYG LNSERSERAR GSERSERGLY GLYGLYGLYS ERSERGLYGL YGLYGLYSER  420
ALAVALTHRL EUASPGLUSE RGLYGLYGLY LEUGLNTHRP ROGLYGLYGL YLEUSERLEU  480
VALCYSLYSA LASERGLYPH ETHRPHESER SERTYRALAM ETASNTRPVA LARGGLNALA  540
PROGLYLYSG LYLEUGLUTR PVALALAALA ILEASPASPA SPGLYSERTY RTHRGLYTYR  600
GLYSERALAV ALLYSGLYAR GALATHRILE SERARGASPA SNGLYGLNSE RTHRVALARG  660
LEUGLNLEUA SNASNLEUAR GALAGLUASP THRALAILET YRTYRCYSAL ALYSALAALA  720
GLYSERGLYT YRCYSTYRAR GGLYALAASN SERSERTYRT HRCYSGLYTH RTYRASNALA  780
GLYASPILEA SPALATRPGL YHISGLYTHR GLUVALILEV ALSERSERTH RSERGLYPRO  840
GLYGLYPROG LUPROLYSSE RSERASPLYS THRHISTHRC YSPROPROCY SPROALAPRO  900
GLULEULEUG LYGLYPROSE RVALPHELEU PHEPROPROL YSPROLYSAS PTHRLEUMET  960
ILESERARGT HRPROGLUVA LTHRCYSVAL VALVALASPV ALSERHISGL UASPPROGLU 1020
VALLYSPHEA SNTRPTYRVA LASPGLYVAL GLUVALHISA SNALALYSTH RLYSPROARG 1080
GLUGLUGLNT YRASNSERTH RTYRARGVAL VALSERVALL EUTHRVALLE UHISGLNASP 1140
TRPLEUASNG LYLYSGLUTY RLYSCYSLYS VALSERASNL YSALALEUPR QALAPROILE 1200
GLULYSTHRI LESERLYSAL ALYSGLYGLN PROARGGLUP ROGLNVALTY RTHRLEUPRO 1260
PROSERARGA SPGLULEUTH RLYSASNGLN VALSERLEUT HRCYSLEUVA LLYSGLYPHE 1320
TYRPROSERA SPILEALAVA LGLUTRPGLU SERASNGLYG LNPROGLUAS NASNTYRLYS 1380
THRTHRPROP ROVALLEUAS PSERASPGLY SERPHEPHEL EUTYRSERLY SLEUTHRVAL 1440
ASPLYSSERA RGTRPGLNGL NGLYASNVAL PHESERCYSS ERVALMETHI SGLUALALEU 1500
HISASNHIST YRTHRGLNLY SSERLEUSER LEUSERPROG LYLYS               1545

SEQ ID NO: 13           moltype = DNA  length = 1548
FEATURE                 Location/Qualifiers
misc_feature            1..1548
                        note = anti-PROX1-scFv-hFc
source                  1..1548
                        mol_type = other DNA
                        organism = synthetic construct
SEQUENCE: 13
atggagacag acacactcct gctatgggta ctgctgctct tagcggccca gccggccctg   60
actcagccgt cctcggtgtc agcaaaccta ggagaaaccg tcgagatcac ctgctccggg  120
ggtagtggca gctatggctg gtatcagcag aagtcacctg gcagtgcccc tgtcactctg  180
atctatgaca acgccaacag accctcgaac atcccttccg gattctccgg ttccaaatcc  240
ggctccacgg gcacattaac catcactggg gtccgagccg aggatgaggc tgtctattac  300
tgtgggaatg tagacagcag cacttatgtt ggtatgtttg gggccgggac aaccctgacc  360
gtcctaggtc agtcctctag atcttccggc ggtggtggca gctccggtgg tggcggttcc  420
gccgtgacgt tggacgagtc cggggcggc ctccagacgc ccggaggagg gctcagcctc  480
gtctgcaagg cctccgggtt caccttcagc agttatgcca tgaactgggt gcgacaggcc  540
cccggcaagg ggctggagtg ggtcgctgct attgatgatg atggtagtta cacaggctac  600
gggtcggcgg tgaaggcccg tgccaccatc tcgagggaca cgggcagag cacagtgagg  660
ctgcagctga caacctcag ggctgaggac accgccatct actactgcgc caaagctgct  720
ggtagtggtt actgttatcg tggtgctaat agtagttata cttgtggtac ttataacgct  780
ggtgacatcg acgcatgggg ccacgggacc gaagtcatcg tctcctccac tagtggcccg  840
ggaggccccg agcccaaatc ttctgacaaa actcacacat gcccaccgtg cccagcacct  900
gaactcctgg gggaccgtc agtcttcctc ttccccccaa aacccaagga cacccctcatg  960
atctcccgga cccctgaggt cacatgcgtg gtggtggacg tgagccacga agaccctgag 1020
gtcaagttca actggtacgt ggacggcgtg gaggtgcata atgccaagac aaagccgcgg 1080
gaggagcagt acaacagcac gtaccgtgtg gtcagcgtcc tcaccgtcct gcaccaggac 1140
tggctgaatg gcaaggagta caagtgcaag gtctccaaca agcccctccc cccccccatc 1200
gagaaaacca tctccaaagc caaagggcag ccccgagaac cacaggtgta ccccctgccc 1260
ccatccccgg atgagctgac caagaaccag gtcagcctga cctgcctggt caaaggcttc 1320
tatcccagcg acatcgccgt ggagtgggag agcaatgggc agccggagaa caactacaag 1380
accacgcctc ccgtgctgga ctccgacggc tccttcttcc tctatagcaa gctcaccgtg 1440
gacaagagca ggtggcagca ggggaacgtc ttctcatgct ccgtgatgca tgaggctctg 1500
cacaaccact acacgcagaa gagcctctcc ctgtctccgg gtaaatga               1548

SEQ ID NO: 14           moltype = AA   length = 882
FEATURE                 Location/Qualifiers
REGION                  1..882
                        note = AAV2/2-IL2'SP-anti-PROX1-scFv-Flag
source                  1..882
                        mol_type = protein
                        organism = synthetic construct
SEQUENCE: 14
METTYRARGM ETGLNLEULE USERCYSILE ALALEUEUVA LTHRASNSER              60
METLEUTHRG LNPROSERSE RVALSERALA ASNLEUGLYG LUTHRVALGL UILETHRCYS  120
SERGLYGLYS ERGLYSERTY RGLYTRPTYR GLNGLNLYSS ERPROGLYSE RALAPROVAL  180
THRLEUILET YRASPASNAL AASNARGPRO SERASNILEP ROSERARGPH ESERGLYSER  240
LYSSERGLYS ERTHRGLYTH RLEUTHRILE THRGLYVALA RGALAGLUAS PGLUALAVAL  300
TYRTYRCYSG LYASNVALAS PSERSERTHR TYRVALGLYM ETPHEGLYAL AGLYTHRTHR  360
LEUTHRVALL EUGLYGLNSE RSERARGSER SERGLYGLYG LYGLYSERSE RGLYGLYGLY  420
GLYSERALAV ALTHRLEUAS PGLUSERGLY GLYGLYLEUG LNTHRPROGL YGLYGLYLEU  480
SERLEUVALC YSLYSALASE RGLYPHETHR PHESERSERT YRALAMETAS NTRPVALARG  540
```

```
GLNALAPROG  LYLYSGLYLE  UGLUTRPVAL  ALAALAILEA  SPASPASPGL  YSERTYRTHR   600
GLYTYRGLYS  ERALAVALLY  SGLYARGALA  THRILESERA  RGASPASNGL  YGLNSERTHR   660
VALARGLEUG  LNLEUASNAS  NLEUARGALA  GLUASPTHRA  LAILETYRTY  RCYSALALYS   720
ALAALAGLYS  ERGLYTYRCY  STYRARGGLY  ALAASNSERS  ERTYRTHRCY  SGLYTHRTYR   780
ASNALAGLYA  SPILEASPAL  ATRPGLYHIS  GLYTHRGLUV  ALILEVALSE  RSERTHRSER   840
GLYGLNALAG  LYGLNMETAS  PTYRLYSASP  ASPASPASPL  YS                      882

SEQ ID NO: 15           moltype = DNA   length = 888
FEATURE                 Location/Qualifiers
misc_feature            1..888
                        note = AAV2/2-IL2'SP-anti-PROX1-scFv-Flag
source                  1..888
                        mol_type = other DNA
                        organism = synthetic construct
SEQUENCE: 15
atgtacagaa  tgcaactcct  gtcttgtatt  gcactaagtc  tcgcacttgt  cacaaacagt   60
atgctgactc  agccgtcctc  ggtgtcagca  aacctaggag  aaaccgtcga  gatcacctgc  120
tccggggta   gtggcagcta  tggctggtat  cagcagaagt  cacctggcag  tgccctgtc   180
actctgatct  atgacaacgc  caacagaccc  tcgaacatcc  cttcacgatt  ctccggttcc  240
aaatccggct  ccacgggcac  attaaccatc  actggggtcc  gagccgagga  tgaggctgtc  300
tattactgtg  ggaatgtaga  cagcagcact  tatgttggta  tgtttgggc   cgggacaacc  360
ctgaccgtcc  taggtcagtc  ctctagatct  tccggcggtg  gtggcagctc  cggtggtggc  420
ggttccgccg  tgacgttgga  cgagtccggg  ggcggcctcc  agacgccgg   aggagggctc  480
agcctcgtct  gcaaggcctc  cgggttcacc  ttcagcagtt  atgccatgaa  ctgggtgcga  540
caggcgcccg  gcaaggggct  ggagtgggtc  gctgctattg  atgatgatgg  tagttacaca  600
ggctacgggt  cggcggtgaa  gggccgtgcc  accatctcga  gggacaacgg  gcagagcaca  660
gtgaggctgc  agctgaacaa  cctcagggct  gaggacaccg  ccatctacta  ctgcgccaaa  720
gctgctggta  gtggttactg  ttatcgtggt  gctaatagta  gttatacttg  tggtacttat  780
aacgctggtg  acatcgacgc  atggggccac  gggaccgaag  tcatcgtctc  ctccactagt  840
ggccaggccg  gccagatgga  ctacaaagac  gatgacgaca  agtagtag               888
```

BINDING MOLECULE ABLE TO NEUTRALIZE PROX1 PROTEIN

RELATED APPLICATIONS

The present invention is a U.S. Nonprovisional Patent Application, claiming priority to Korean Patent Application No. 10-2021-0190878, filed on Dec. 29, 2021; the entirety of which is hereby incorporated herein by reference.

TECHNICAL FIELD

The present disclosure relates to binding molecules with neutralizing activity on PROX1 proteins. More specifically, the binding molecules of the present disclosure relate to binding molecules that have excellent binding ability to PROX1 proteins and have excellent neutralizing effects on PROX1 proteins.

BACKGROUND

The retina is a transparent nerve tissue that covers the innermost part of the eyeball, and light entering the eye passes through the inner layer of the retina and is detected by the optic cells of the retina. Optic cells convert light information back into electrical information, which passes through neurons and optic nerves in the inner layer of the retina to the brain, where it is possible to see objects. The outermost part of the eye is the avascular fibrous layer (cornea, sclera), and the middle layer is the uvea (iris, ciliary body, choroid), which is vascular tissue, and the transparent nerve tissue covering the inside of the choroid, the middle layer, is the retina. The retina is a thin transparent membrane of different thicknesses, and depending on its location, the middle core of the retina is further divided into the central fossa, the vicina of the fossa, and the periscle. The central fossa is clinically called the macula.

On the other hand, retinal neurodegenerative diseases can occur due to congenital or acquired damage to the retina, or complications of chronic diseases such as hypertension and diabetes, specifically, Retinitis Pigmentosa, which shows night blindness as an early symptom, and a hereditary retinal abnormality, which is congenital retinal degeneration diseases such as Leber Congenital Amaurosis (LCA), Retinal Detachment in which the retina tears and falls off, Diabetic retinopathy caused by diabetes, central retinopathy, and senile retinal degeneration. These diseases cause symptoms such as decreased visual acuity, visual impairment, night blindness, color weakness, color blindness, photopsia (flashing lights appear when the eyes are moved), epistaxis (seeing something floating in front of the eyes), deformation (the appearance of curved objects), and scotoma (black appearance of the center of vision). However, unlike lower vertebrates, which can regenerate retinal neurons, retinal neurons do not regenerate in mammals and are nerve tissues that cannot be transplanted, so once the retina is damaged, it cannot be repaired, which can lead to blindness as a result.

Despite the rapid increase in incidence of these retinal neurodegenerative diseases, there are currently few effective treatments. Recently, research on cell therapy using various stem cells has been conducted to replace and protect retinal cells, but it has not yet been applied clinically (Korean registered patent, 10-1268741), and Stargardt's disease gene therapy targeting retinal pigment epithelial cells has been applied to clinical practice, but this is limited to patients with some gene mutations, and there is currently no technology that can restore visual function by regenerating the degenerated retina.

In addition, it was confirmed that the movement of PROX1 protein to Müller glia in the damaged mammalian retina was induced to induce division of Müller glia, thereby showing the regenerative effect of retinal neurons, but research on anti-PROX1 antibodies having a neutralizing effect that directly binds to PROX1 protein in vivo and inhibits function is still insufficient.

Therefore, there is a need to develop safe and effective therapeutics that can be widely applied to various diseases caused by retinal degeneration in mammals including humans, which are fundamentally incapable of retinal nerve regeneration.

SUMMARY

In order to solve the above problem, the present researchers have developed a molecule having binding ability to the PROX1 (Prospero homeobox protein 1) protein, and the binding molecule has excellent binding power and/or a neutralizing effect on the PROX1 protein, and the present disclosure has been completed.

One aspect is to provide an antibody or fragment thereof, which specifically binds to the PROX1 protein.

Another aspect is to provide an immunoconjugate in which one or more tags are additionally bound to the antibody or binding fragment thereof.

Another aspect is to provide a nucleic acid molecule encoding the antibody or binding fragment thereof.

Another aspect is to provide an expression vector into which the nucleic acid molecule is inserted.

Another aspect is to provide a composition for the prevention or treatment of retinal neurodegenerative diseases, comprising the antibody or binding fragment thereof.

Another aspect is to provide a kit for the prevention or treatment of retinal neurodegenerative diseases, comprising the antibody or binding fragment thereof.

Another aspect is to provide adeno-associated virus expressing the antibody or binding fragment thereof.

The present disclosure provides a molecule that specifically binds to the PROX1 protein.

The binding molecule of the present disclosure may exhibit excellent neutralizing ability while having excellent binding ability to PROX1 protein. By way of one embodiment, the binding molecule of the present disclosure is screened as a molecule that binds to the PROX1 protein and exhibits neutralizing ability but is not limited thereto.

In the present disclosure, the PROX1 protein encoded by the gene of PROX1 (Prospero homeobox protein 1) is a type of homeoprotein and includes a homeodomain composed of a 60-amino acid helix-turn-helix structure that binds to DNA and RNA. The protein is conserved in vertebrates and is known to play various roles in the development of the liver, retina, lymphatic system, etc. In particular, it is reported to have all functions of controlling the proliferation of cells, allowing cells to move to appropriate positions, and differentiating the cells to have unique functions. In addition, changes in the level of the protein have been reported in cancers occurring in tissues such as the colon, brain, blood, breast, pancreas, liver, and esophagus. In mammalian retina, PROX1 protein is expressed in neurons in the retina. PROX1 protein is also detectable in Müller glia, in which PROX1 protein is known to be present in very small amounts.

In the present disclosure, the term "homeodomain" refers to a protein with a structure that exhibits gene binding activity composed of about 60 amino acids. The homeodomain is expressed from a gene of 180 bp in size known as a homeobox. It can function by binding sequence-specific to the target gene promoter site to promote or inhibit gene expression.

In one embodiment of the disclosure, the binding molecule may be a binding molecule that specifically binds to the homeodomain region on the PROX1 protein.

In the present disclosure, the Müller glia is a type of retinal glia first discovered by Heinrich Müller and is a support cell of neurons in the retina of vertebrates. It is known that the Müller glia can divide and differentiate to neurons upon the injuries of fish retina. However, retinal neuronal regeneration does not occur in the retina of mammals because the cell division of Müller glia is inhibited.

As used herein, the term "binding molecule" includes an immunoglobulin including a monoclonal antibody, such as a chimeric, humanized, or human monoclonal antibody, or an antigen-binding fragment of an immunoglobulin that binds to an antigen. For example, in binding with the PROX1 protein, it means a variable domain of an immunoglobulin fragment competing with an intact immunoglobulin. Regardless of structure, the antigen-binding fragment binds to the same antigen recognized by the intact immunoglobulin. An antigen-binding fragment may include a peptide or polypeptide consists of two or more consecutive groups of the amino acid sequence of an antibody, more than 20 consecutive amino acid residues, 25 or more consecutive amino acid residues, more than 30 consecutive amino acid residues, 35 or more consecutive amino acid residues, 40 or more consecutive amino acid residues, 50 or more consecutive amino acid residues, 60 or more consecutive amino acid residues, 70 or more consecutive amino acid residues, 80 or more consecutive amino acid residues, 90 or more consecutive amino acid residues, 100 or more consecutive amino acid residues, 125 or more consecutive amino acid residues, 150 or more consecutive amino acid residues, 175 or more consecutive amino acid residues, 200 or more consecutive amino acid residues, or 250 or more consecutive amino acid residues.

When the PROX1 protein-binding molecule of the present disclosure is used to inhibit the accumulation of PROX1 protein in Müller glia that appears during in the injured retina of mammals. The suppression of the accumulation of PROX1 protein in Müller glia can promote regeneration of retinal neurons via the promotion of the division of Müller glia and/or Müller glia-derived retinal neural progenitor cell. In addition, when inhibiting the accumulation of PROX1 protein in Müller glia using the PROX1 protein binding molecule, it may be effective by inhibiting the proliferation of microglia that induces phagocytosis and inflammatory response.

In the present disclosure, a binding molecule specifically binding to the PROX1 protein can inhibit the intercellular migration of the PROX1 protein. It may specifically bind to the PROX1 protein or competitively inhibit the binding of the PROX1 protein to the Müller glial cell membrane but is not limited thereto.

In one embodiment of the present disclosure, the binding molecule that specifically binds to the PROX1 protein may be anyone selected from the group consisting of antibodies, peptides, peptide analogs, aptamers, and compounds that specifically bind to the PROX1 protein or competitively inhibit binding to the PROX1 protein and the Müller glial cell membrane. Specifically, the binding molecule may be an antibody or a binding fragment thereof.

In this specification, 'antibody' is used in the broadest sense possible, and specifically includes intact monoclonal antibodies, polyclonal antibodies, multispecific antibodies (e.g., bispecific antibodies) formed from two or more intact antibodies, and antibody fragments exhibiting the desired biological activity. An antibody is a protein produced by the immune system that can recognize and bind to a specific antigen. In its structural terms, the antibody typically has a Y-shaped protein consisting of four amino acid chains (two heavy chains and two light chains). Each antibody has two regions, mainly a variable region and a constant region. The variable region located at the distal end of the arm of Y binds to and interacts with the target antigen. The variable region includes a complementarity-determining region (CDR) that recognizes and binds to a specific binding site on a particular antigen. The constant region located at the tail of Y is recognized and interacted with by the immune system. The target antigen has several binding sites called epitopes, which are generally recognized by CDRs on multiple antibodies. Each antibody that specifically binds to a different epitope has a different structure. Therefore, one antigen may have one or more corresponding antibodies.

In one embodiment of the invention, a PROX1 neutralizing antibody was administrated to inhibit the migration of PROX1 protein to Müller glia in the injured mouse retina. The neutralizing activity of a PROX1 neutralizing antibody was confirmed that the level of PROX1 protein in Müller glia did not increase. Through this, it was confirmed that the division of Müller glia can be induced by inhibiting the migration of PROX1 protein to Müller glia through injection of PROX1 neutralizing antibody in the eye. The administration of a PROX1 neutralizing antibody can induce regeneration of retinal neurons from the Müller glia-derived cells in the future.

In one embodiment of the invention, the antibody or binding fragment thereof includes a) a light chain variable region described as SEQ ID NO: 3; and b) a heavy chain variable region described as SEQ ID NO: 4. In this case, it may include a sequence having 70% or more, preferably at least 80%, more preferably at least 90%, most preferably 95, 96, 97, 98, 99% or more, sequence homology with the amino acid sequence represented by SEQ ID NO: 3 or SEQ ID NO: 4.

In one embodiment of the invention, the antibody or binding fragment thereof comprises a) a CDR1 region described as SEQ ID NO: 6, a CDR2 region described as SEQ ID NO: 7, and a CDR3 region described as SEQ ID NO: 8; and b) a heavy chain variable region including a CDR1 region described as SEQ ID NO: 9, a CDR2 region described as SEQ ID NO: 10, and a CDR3 region described as SEQ ID NO: 11. In this case, it may include a sequence having 70%, preferably at least 80%, more preferably at least 90%, most preferably 95, 96, 97, 98, 99% or more, sequence homology with the amino acid sequence represented by SEQ ID NOS: 6 to 11.

In one embodiment of the invention, the binding molecule may be, but is not limited to, scFv fragments, scFv-Fc sections, Fab fragments, Fv fragments, diabodies, chimeric antibodies, humanized antibodies, or human antibodies.

One embodiment of the present disclosure provides scFv-Fc binding to a PROX1 protein.

In addition, another embodiment of the present disclosure provides a humanized single chain antibody (scFv-hFc) that binds to the PROX1 protein.

In addition, the present disclosure includes functional variants of the binding molecule. Binding molecules are considered functional variants of binding molecules of the invention if the variants can compete with binding molecules of the invention to specifically bind to PROX1 proteins and possess neutralization capabilities for PROX1 proteins. Functional variants include, but are not limited to, derivatives whose primary structural sequences are substantially similar, including, for example, in vitro or in vivo modifications, chemicals and/or biochemical agents, they are not found in the parent antibodies of the invention. Such modifications include, for example, acetylation, acylation, covalent bonding of nucleotides or nucleotide derivatives, covalent bonds of lipids or lipid derivatives, crosslinking, disulfide bond formation, glycosylation, hydroxylation, methylation, oxidation, pegylation, proteolysis, and phosphorylation. The functional variant may optionally be an antibody including an amino acid sequence containing substitution, insertion, deletion, or combination thereof of one or more amino acids compared to the amino acid sequence of the parent antibody. Moreover, functional variants may include truncated forms of amino acid sequences at one or both amino terminus or carboxy terminus. Functional variants of the disclosure may have the same, different, higher, or lower binding affinity compared to the parent antibodies of the disclosure but can still bind to the PROX1 protein. For example, the amino acid sequence of a variable region, including but not limited to, a skeletal structure, a hypervariable region, in particular a complementarity-determining region (CDR) of a light or heavy chain may be modified. In general, the light or heavy chain region includes three CDR regions, it includes three hypervariable regions and a more conserved region, i.e., a framework region (FR). The hypervariable region includes amino acid residues from CDR and amino acid residues from the hypervariable loop. Functional variants within the scope of the present disclosure may have about 50%~99%, about 60%~99%, about 80%~99%, about 90%~99%, about 95%~99%, or about 97%~99% amino acid sequence homogeneity with the parent antibodies of the present specification. Among computer algorithms known to those skilled in the art, Gap or Bestfit can be used to optimally align amino acid sequences to be compared and define similar or identical amino acid residues. Functional variants can be obtained by changing the parent antibody or part thereof by known general molecular biology methods including PCR, mutagenesis using oligomeric nucleotides and partial mutagenesis, or obtained by organic synthesis, but are not limited thereto.

In addition, the present disclosure provides an immunoconjugate to which one or more tags are additionally bound to the binding molecule. Specifically, the immunoconjugate may be an immunoconjugate in which one or more tags are additionally bound to an antibody or binding fragment thereof.

In one embodiment of the present disclosure, the tag may be a hexa-histidine (His) tag, a hemagglutinin (HA) tag, an Myc tag, a V5 tag, or an F lag tag. Specifically, the tag may be a hexa-histidine tag.

In one embodiment, the drug may be further attached to the binding molecule. That is, the binding molecule according to the present disclosure can be used in the form of an antibody-drug conjugate to which the drug is bound. When an antibody-drug conjugate (ADC), i.e., an immunoconjugate, is used to deliver the drug topically, the drug moiety can be targeted and delivered to infected cells, and if the drug agent is administered without conjugation, an unacceptable level of toxicity may be caused even for normal cells. Drug-connectivity and drug-release, as well as polyclonal and monoclonal by increasing the selectivity of antibodies (mAbs), the maximum efficacy and minimum toxicity of ADCs can be improved.

Conventional means of attaching drug moieties to antibodies, i.e., linking them through covalent bonds, generally result in heterogeneous molecular mixtures in which drug moieties are attached to numerous sites on the antibody. For example, cytotoxic drugs can typically be conjugated with antibodies, often through numerous lysine residues of the antibody, to produce an inhomogeneous antibody-drug conjugate mixture. Depending on the reaction conditions, such heterogeneous mixtures typically have an antibody distribution degree of 0 to about 8 or more attached to the drug moiety. In addition, each subgroup of conjugates with special integer ratio drug moieties versus antibodies is a potentially inhomogeneous mixture in which drug moieties are attached to various sites on the antibody. Antibodies are large, complex, and structurally diverse biomolecules, often with many reactive functional groups. Reactivity with linker reagents and drug-linker intermediates depends on factors such as pH, concentration, salt concentration, and quiet medium.

In addition, the present disclosure provides a nucleic acid molecule encoding the binding molecule. Specifically, the nucleic acid molecule may be a nucleic acid molecule encoding the antibody or binding fragment thereof.

The nucleic acid molecules of the present disclosure include all nucleic acid molecules translated into polynucleotide sequences as the amino acid sequences of antibodies provided in the present disclosure are known to those skilled in the art. Therefore, various polynucleotide sequences can be prepared by an open reading frame (ORF), all of which are also included in the nucleic acid molecules of the present disclosure.

In one embodiment of the disclosure, the nucleic acid molecule may include a DNA sequence represented by SEQ ID NO: 2 or a DNA sequence represented by SEQ ID NO: 13.

In addition, the present disclosure provides a vector into which the nucleic acid molecule is inserted. In one embodiment of the disclosure, the vector is an expression vector or a viral vector, for example, the viral vector is a retroviral vector, an adenoviral vector, a vaccinal virus or an adeno-associated viral vector.

The expression vectors include Celltrion's own expression vector, MarEx vector (see Korean Patent Registration No. 10-1076602), and commercially widely used pCDNA, pCAG, pET, F, R1, RP1, Col, pBR322, ToL, Ti vectors; cosmid; phages such as lambdas, lambdoids, M13, Mu, p1 P22, Qμ, T-even, T2, T3, T7, and the like; and any expression vector selected from the group consisting of plant viruses can be used, but is not limited thereto, and all expression vectors known to those skilled in the art as expression vectors are available to the present disclosure, and when selecting an expression vector, it depends on the characteristics of the host cell of interest. Transfection of vectors into host cells may be performed by calcium phosphate transfection, viral infection, DEAE-dextran controlled transfection, lipofectamine transfection or electroporation, but is not limited thereto, those skilled in the art can select and use an introduction method suitable for the expression vector and host cell to be used. For example, vectors contain one or more selectable markers, but are not limited thereto, and vectors without selectable markers can also be used for selection depending on whether a product is produced. selection markers are selected by the desired host cell, which uses methods already known to those skilled in the art, so the present disclosure does not limit thereto.

In order to facilitate purification of the binding molecules of the present disclosure, the tag sequence can be inserted onto the expression vector and fused.

The tags include, but are not limited to, hexa-histidine tags (His), hemagglutinin tags (HA), Myc tags, V5 tags or Flag tags, and tags that facilitate purification known to those skilled in the art are all available in the present disclosure.

In addition, the present disclosure provides a composition for the prevention or treatment of retinal neurodegenerative diseases including antibodies or binding fragments thereof that bind to the PROX1 protein.

The antibody or fragment thereof of the present disclosure can exhibit a therapeutic effect on a disease caused by damage or degeneration of retinal neurons in mammals through inhibition of the accumulation of PROX1 protein in Müller glia that appears during retinal nerve injury.

The composition of the present disclosure may promote the regeneration of retinal neurons from the Müller glia-derived cells. The composition of the present disclosure may promote the regeneration of retinal neurons by inhibiting the proliferation of microglia cells inducing inflammatory response.

In the present invention, the retinal nerve degenerative disease may be any one selected from the group consisting of Retinitis Pigmentosa, Leber Congenital Amaurosis (LCA), Retinal Detachment (RD), macular degeneration, diabetic retinopathy, glaucoma, central retinopathy, and senile retinal degeneration, but is not limited thereto.

The term "prevention" used herein means any act of inhibiting or delaying the onset of a retinal neurodegenerative disease by administration of a pharmaceutical composition according to the present disclosure.

As used herein, the term "treatment" refers to any action in which the symptoms of a retinal neurodegenerative disease are improved or beneficially altered by administration of a pharmaceutical composition according to the present disclosure.

The composition according to the present disclosure may be used alone or in combination with surgery, radiotherapy, chemotherapy and biological response modulators for the prevention or treatment of retinal neurodegenerative diseases, preferably in combination with drugs that promote differentiation of neurons.

The composition according to the present disclosure may further include a pharmaceutically acceptable carrier. The pharmaceutically acceptable carrier is commonly used in formulations, including saline, sterile water, Ringer's solution, buffer saline, cyclodextrin, dextrose solution, maltodextrin solution, glycerol, ethanol, liposomes, and the like, but is not limited to, and may further include other conventional additives such as antioxidants and buffers as needed. Also, diluents, dispersants, surfactants, binders, lubricants, etc. may be additionally added, injectable formulations such as aqueous solutions, suspensions, emulsions, etc., injections such as infusion bags, sprays such as aerosol formulations, pills, capsules, granules or tablets may be formulated. As for suitable pharmaceutically acceptable carriers and formulations, the methods disclosed in Remington's literature can preferably be formulated according to each component. The pharmaceutical formulations of the present disclosure have no particular limitation in formulation, but may be formulated as injectables, injections, spray formulations, liquid formulations, or external skin agents.

The compositions of the present disclosure may be administered orally or parenterally (e.g., applied to a topical including intraocular, intravenous, subcutaneous, or intraperitoneal) according to the desired method, and the dosage may vary depending on the patient's condition and weight, degree of disease, drug form, route of administration and time, but may be appropriately selected by those skilled in the art.

The composition of the present disclosure can be administered in a pharmaceutically effective amount. In the present disclosure, "pharmaceutically effective amount" means an amount sufficient to treat or diagnose a disease at a reasonable benefit/risk ratio applicable to medical treatment or diagnosis, and the effective dose level is the patient's disease type, severity, activity of the drug, sensitivity to the drug, administration time, route of administration and discharge rate, treatment period, factors including drugs used at the same time, and other well-known factors in the medical field. The composition according to the present invention may be administered as an individual therapeutic agent or in combination with other therapeutic agents, may be administered sequentially or simultaneously with conventional therapeutic agents, and may be administered single or multiple times. Considering all of the above factors, it is important to administer the amount that can obtain the maximum effect with the minimum amount without side effects, which can be easily determined by those skilled in the art.

Specifically, the effective amount of the composition of the present disclosure may vary depending on the age, sex, condition, weight, absorption of the active ingredient in the body, inactivity rate and excretion rate, disease type, and concomitant drugs, and generally 0.001 to 150 mg per 1 kg of body weight, preferably 0.01 to 100 mg daily or alternate, or 1 to 3 times a day. But since it may increase or decrease depending on the administration route, severity of obesity, gender, weight, age, and the like, the dosage does not limit the scope of the present disclosure in any way.

In another aspect of the invention, there is provided a pharmaceutical formulation for the prevention or treatment of retinal neurodegenerative diseases, including the composition.

As an embodiment of the present disclosure, the pharmaceutical formulation may be an injection formulation, an ointment formulation, a spray formulation, a liquid formulation, or a solid formulation.

In another embodiment of the present disclosure, the pharmaceutical formulation may be for ocular topical administration.

The present disclosure also provides kits for the diagnosis, prevention, or treatment of retinal neurodegenerative diseases, including antibodies or binding fragments thereof that bind to the PROX1 protein.

In one embodiment of the invention, the binding molecules of the invention used in diagnostic kits can be detectably marked. Various methods available for marking biomolecules are well known to those skilled in the art and are contemplated within the scope of the present disclosure. Examples of marking types that can be used in the present disclosure include enzymes, radioisotopes, colloidal metals, fluorescent compounds, chemiluminescent compounds, and bioluminescent compounds. Commonly used markers include fluorescent materials (e.g., fluresin, rhodamine, Texas red, etc.), enzymes (e.g., horseradish peroxidase, β-galactosidase, alkaline phosphatase), radioisotopes (e.g., 32P or 125I), biotin, digoxogenin, colloidal metals, chemiluminescent or bioluminescent compounds (e.g., deoxetane, luminol or acridinium). Marking methods such as covalent bonding of enzymes or biotinyl groups, iodination, phosphorylation, biotinization, and the like are well known in the art. Detection methods include, but are not limited to, autoradiography, fluorescence microscopy, direct and indirect enzymatic reactions, and the like. Commonly used detection methods include radioisotope or non-radioisotope methods. These include, among others, Western Blotting, immunoprecipitation (IP), Overlay-Assay, Radioimmuno Assay (RIA), ImmuneRadioimmunometric Assay (IRMA), Enzyme Immuno Assay (EIA), Enzyme Linked Immuno Sorbent Assay (ELISA), Fluorescent Immuno Assay (FIA), and Chemioluminescent Immune Assay (CLIA).

The diagnostic kit of the present disclosure can be used to detect the presence of PROX1 protein by contacting the sample with the binding molecule and then checking the reaction. Since the sample may be anyone selected from the group consisting of sputum, saliva, blood, sweat, lung cells, mucus of lung tissue, respiratory tissue, and saliva of the subject, but is not limited thereto, sample preparation is possible by conventional methods known to those skilled in the art.

One embodiment of the invention includes: a) the binding molecule; and b) a kit including a container.

In the diagnostic, preventive or therapeutic kit of the present disclosure, the kit container may include a solid carrier. The antibodies of the present disclosure may be attached to a solid carrier, and such solid carriers may be porous or non-porous, planar, or non-planar.

In addition, the present disclosure provides an antibody that binds to the PROX1 protein or adeno-associated virus (AAV) expressing a binding fragment thereof.

In one embodiment, the adeno-subvirus may be a) an adeno-attached virus including an amino acid sequence of SEQ ID NO: 14 or b) a DNA sequence of SEQ ID NO: 15.

In addition, the present disclosure provides a method of prevention or treatment of retinal neurodegenerative diseases, including administering to an individual a pharmaceutical composition including an antibody binding to the PROX1 protein or a binding fragment thereof as an active ingredient.

In the present disclosure, "individual" means an object in need of treatment of a disease, and more specifically refers to a human or non-human primate, a mouse, a rat, a dog, a cat, a horse, and a cow or the like.

In addition, in another embodiment of the invention, the present disclosure provides a method of detecting a PROX1 (Prospero homeobox protein 1) protein using the diagnostic kit.

In addition, in another embodiment of the invention, the present disclosure provides a method of diagnosing a retinal neurodegenerative disease using the diagnostic kit.

In addition, the present disclosure provides for the prevention or treatment of retinal neurodegenerative diseases of antibodies or binding fragments thereof that bind to the PROX1 protein.

In addition, the present disclosure provides an application for the preparation of preparations for the prevention or treatment of retinal neurodegenerative diseases of antibodies or binding fragments thereof that bind to the PROX1 protein.

In addition, the present disclosure provides a preventive or therapeutic use of retinal neurodegenerative diseases of compositions including antibodies or binding fragments thereof that bind to the PROX1 protein.

Each of the above features described herein may be used in combination, and the fact that each of the features is described in different subordinate claims does not indicate that they cannot be used in combination.

The binding molecule of the present disclosure has excellent binding ability to PROX1 protein and exhibits an excellent neutralizing effect, so it is very useful for diagnosis, prevention, or treatment of retinal neurodegenerative diseases.

BRIEF DESCRIPTION OF THE DRAWINGS

FIG. 4A is a diagram showing a method of confirming the function of the humanized PROX1 single-chain antibody (anti-PROX1-scFv-hFc) promoting Müller glia cell division by inhibiting the migration of PROX1 protein in vivo.

FIG. 5A shows the production of a second serotype AAV2 (AAV2/2-IL2'SP-anti-PROX1-scFv-Flag) expressing a secreted PROX1 neutralizing single chain antibody, to which the secretion sequence (Signal peptide, SP) of Interleukin 2 (interleukin-2; IL2) is added, and the injection time of AAV2/2-IL2'SP-anti-PROX1-scFv-Flag into the eyes of mice. FIG. 5B is a diagram in which the expression of IL2'SP-anti-PROX1-scFv-Flag in the damaged mouse retina was confirmed by immunofluorescence staining.

FIG. 7 is a diagram illustrating the sequence (clone #1A11) of scFv-His.

FIG. 8 is a diagram illustrating the sequence of scFv-hFc.

FIG. 9 is a diagram showing the sequence of AAV2/2-IL2'SP-anti-PROX1-scFv-Flag.

DETAILED DESCRIPTION

Figure 1:
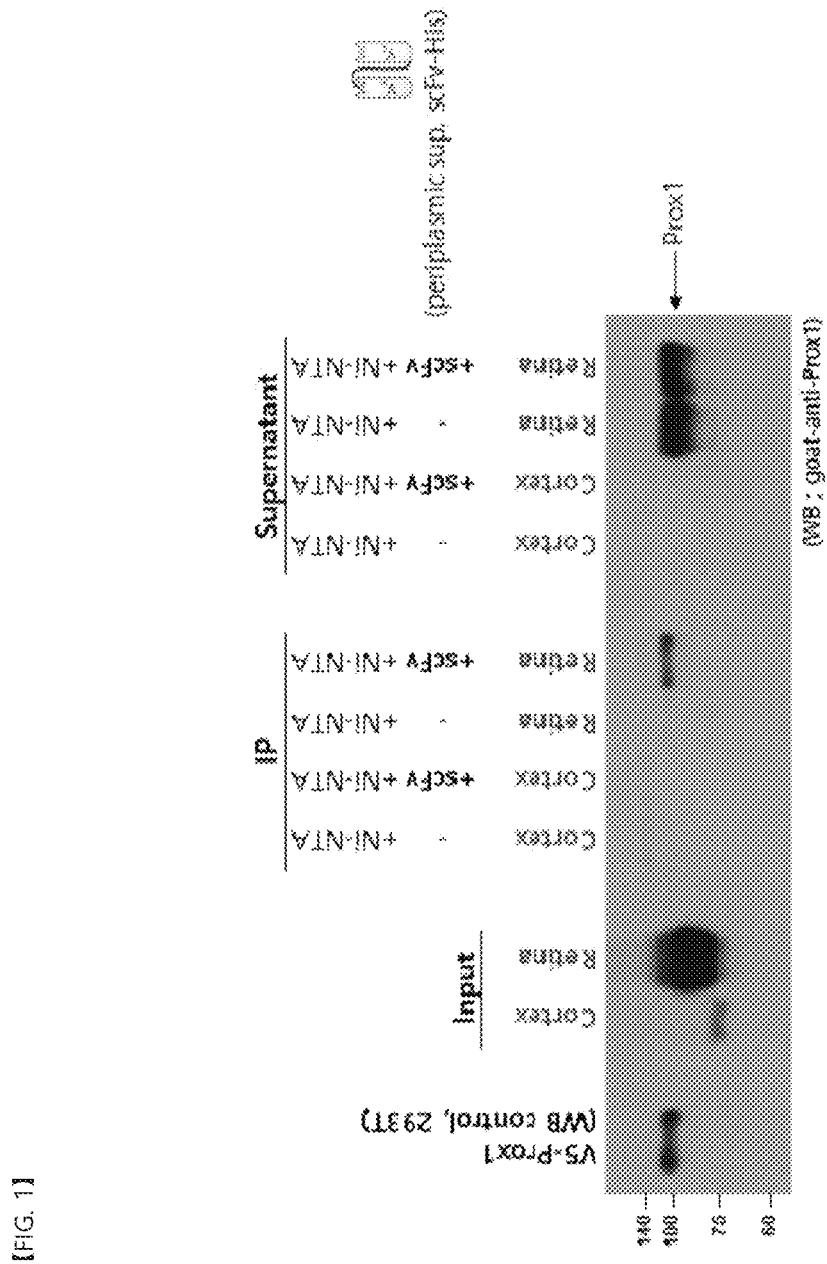
FIG. 1 shows that the neutralizing effect of the PROX1 protein of anti-PROX1 single chain antibody variable region (anti-PROX1-scFv) was confirmed through immunoprecipitation (IP).

Hereinafter, the present disclosure will be described in more detail through embodiments and experimental examples. However, these embodiments are intended to illustrate the present disclosure illustratively, and the scope of the present disclosure is not limited to these embodiments and experimental examples.

EMBODIMENTS AN EXPERIMENTAL EXAMPLES

Experimental Example 1. Experimental Materials and Experimental Methods 1.1. Building an Experimental Mouse The mice used in the experiment were maintained and bred in a mouse facility free of specific pathogens, and all animal experiments performed in this study were conducted according to a protocol (KAIST IACUC 13-130) approved by the Animal Experiment Ethics Committee (IACUC) of the Korea Advanced Institute of Science and Technology (KAIST).

For damage to the eye retina of the mouse, photoreceptor cells were selectively degenerated in the retinas of adult mice by injecting vehicle (PBS containing 0.05% acetic acid) or DNA damaging factor N-Methyl-N-nitrosourea (MNU) (60 mg/kg in the vehicle) into the peritoneal cavity of the mice.

1.2. Cell Culture and Transfection 293T and HeLa cells were maintained in Dulbecco's modified eagle medium (DMEM) containing 10% bovine fetal serum (FBS). The 293T cells were then transfected with polyethylene immigrant (PEI) and HeLa cells were transfected with Genjet DNA in vitro transfection reagent (Signagen) according to the manufacturer's manual.

1.3. Cell Co-Culture

HeLa cells overexpressed with V5-tagged human PROX1 protein (V5-PROX1), or red fluorescent protein (RFP)-tagged Tubulin (RFP-Tubulin) for 24 hours were separated by treatment with Trypisn-EDTA, and the same number of cells were collected in one cell culture plate and co-cultured. From the start of co-culture, PROX1 neutralizing antibody was added to the growth medium of cells and incubated for an additional 24 hours to confirm the effect of inhibiting the movement of PROX1 protein between cells of PROX1 neutralizing antibody.

1.4. Immunocytochemistry (ICC)

HeLa cells co-cultured on a cover slide were fixed in 4% PFA/PBS for 20 minutes and then incubated in a barrier solution (PBS containing 10% normal donkey serum and 0.1% Triton X-100) for 1 hour at room temperature. The cells were then further cultured in a blocking solution including a primary antibody without Triton X-100 (Rabbit-anti-RFP (abcam), Chicken-anti-GFP (abcam), mouse-anti-V5 (GenWay Biotech)) at 4° C. for 16 hours, followed by fluorophore-conjugated secondary antibodies that recognize the primary antibody. Fluorescence images of the ICC signal were then obtained using the Olympus FV1000 confocal microscope.

1.5. Immunoprecipitation (IP)

Immunoprecipitation (IP) experiments were performed to confirm the binding ability of PROX1 protein-binding molecules to PROX1 proteins.

Protein samples were prepared from mice cortex tissue not expressing PROX1 protein and mouse retinal tissue expressing PROX1 protein and PROX1 neutralizing single chain antibody (anti-PROX1-scFv-His) at 4° C. for 16 hours, followed by Ni-NTA beads for 4 hours. Thereafter, the Ni-NTA bead immune complex was washed five times with a washing buffer (50 mM imidazole and protease inhibitor) and a Western blot experiment was performed to confirm the binding ability of the single chain antibody to the PROX1 protein.

1.6. Immunohistochemistry (IHC)

Mouse eyes were isolated for subsequent fixation in PBS containing 4% paraformaldehyde (PFA) for 1 hour. Samples were then transferred to a 20% sucrose/PBS solution for subsequent culture at 4° C. for 16 hours prior to cryopreservation in Tissuetec O.C.T. Frozen mouse eye tissue sections (20 μm) were incubated in a blocking solution (PBS containing 10% donkey serum and 0.1% Triton X-100) for 1 hour at room temperature. Next, the tissue fragments were treated with a blocking solution containing a primary antibody without Triton X-100 added and incubated at 4° C. for 16 hours (Rb-anti-Prox1 (milipore), EdU-cy5 (invitrogen), Rabbit-anti-Iba1 (Wako), Goat-anti-Sox2 (R&D), mouse-anti-Flag (sigma)). The fluorophore-conjugated secondary antibody was then treated and cultured, and then the fluorescence signal of the tissue section was observed and analyzed with the Olympus FV1000 confocal microscope.

Experimental Example 2. Fabrication of Single-Chain Antibodies (scFv-his), Humanized Single-Chain Antibodies (scFv-hFc), and Secretory PROX1 Neutralizing Antibody-Expressing Adeno-Associated Viruses (AAVs)

In the following method, single-chain antibodies (scFv-His), humanized single-chain antibodies (scFv-hFc), and secretory PROX1 single-chain antibody-expressing adeno-associated viruses (AAVs) were produced.

Example 1. His-Tagged Single-Chain Antibody (scFv-his) Production

One anti-PROX1-single chain Fv-His, anti-PROX1-scFv-His, capable of binding to the antigen, was obtained through chicken antibody phage display screening with a C-terminal recombinant protein including the homeodomain of the PROX1 protein (clone #1A11) (see FIG. 1).

FIG. 7 shows the sequence for scFv-His (clone #1A11).

Example 2. Humanized Single Chain Antibody (scFv-hFc)

In addition, in order to enable expression of the PROX1 single-chain antibody (anti-PROX1-scFv) in the mammalian cell line, and at the same time to make them bivalent to form a more effective and more stable structure, the single-chain antibody was cloned with TGEX-SCblue vectors (Antibody Design Laboratories) to add the Fc site of human IgG to produce a humanized PROX1 single-chain anti-chain (anti-PROX1-scFv-hFc).

Specifically, humanized PROX1 single-chain antibodies were overexpressed in 293 T cells and maintained in Dulbecco's modified eagle medium (DMEM) containing 10% bovine fetal serum (FBS). To confirm the production of humanized PROX1 single-chain antibodies, the growth medium of cells was replaced with FreeStyle serum-free media (GIBCO BRL) and collected after 3 days of incubation. The collected culture medium was centrifuged for 1 hour under 2,400 g and 4° C. conditions to obtain a supernatant fraction containing PROX1 neutralizing antibody. By filter sterilization using a 0.22-um-pore-size filter, the final humanized PROX1 single-chain antibody was obtained (see FIG. 2).

FIG. 8 shows the sequence for scFv-hFc.

Figure 2:
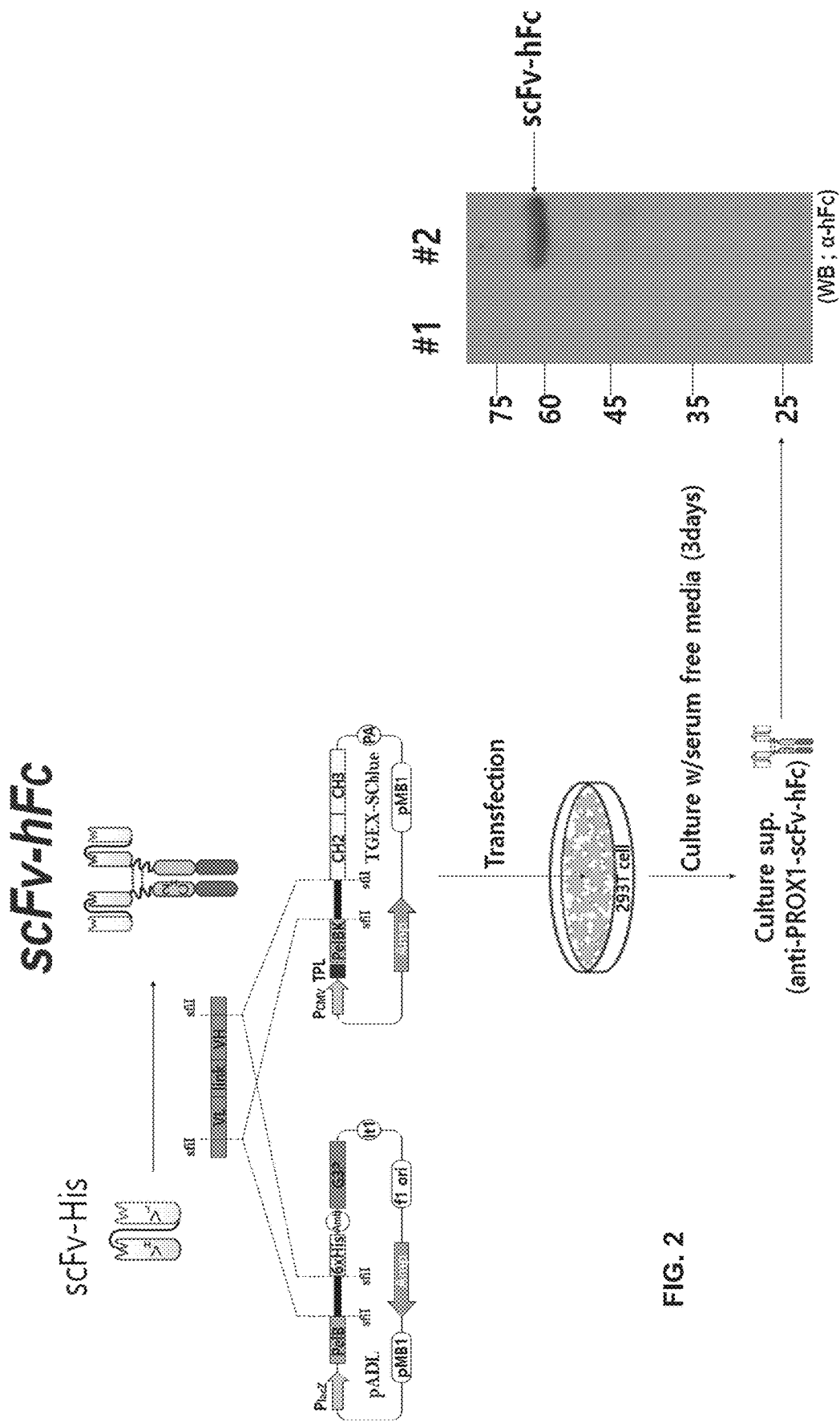
FIG. 2 shows a humanized PROX1 single-chain antibody (anti-PROX1-scFv-hFc) preparation method and the prepared single-chain antibody confirmed through a Western blot.

It was confirmed through Western blot experiments for detecting hFc in cell culture medium (#1; 30 μl of culture medium of control cells, #2; 30 μl of culture medium of cells overexpressing PROX1 single-chain antibody-hFc) that the humanized PROX1 single-chain antibody (anti-PROX1-scFv-hFc) was normally produced (see FIG. 2).

Example 3. PROX1 Neutralizing Single-Chain Antibody-Expressing Adeno-Associated Virus (AAV) Production In addition, in order to overcome the problem of low tissue penetration of antibody protein therapeutics and maintain the neutralizing antibody effect for a long time, this laboratory sought to express the newly secured PROX1 single-chain antibody (anti-PROX1-scFv) in tissues using an adeno-associated virus (AAV).

A second serotype AAV2 (AAV2/2-IL2'SP-anti-PROX1-scFv-Flag, 8.9×10$^{10}$ Genome Copies/µl) was constructed by cloning the interleukin 2(IL2) secretion sequence (signal peptide, SP) and the Flag marker.

FIG. 9 shows the sequence for AAV2/2-IL2'SP-anti-PROX1-scFv-Flag.

Experimental Example 3. Confirmation of His-Tagged Single-Chain Antibody's Binding Ability to the PROX1 Protein Immunoprecipitation (IP) experiments were performed to confirm the binding ability of one His-tagged single chain antibody (anti-PROX1-single chain Fv-His, anti-PROX1-scFv-His) obtained through a chicken antibody phage library search with PROX1 protein.

Protein samples were prepared from mice cortex tissue that did not express PROX1 protein and mouse retinal tissue expressing Prox1 protein, and phage periplasmic supernatant containing His-tagged single-chain antibodies were incubated at 4° C. for 16 hours, followed by Ni-NTA beads for 4 hours. Thereafter, the Ni-NTA bead immune complex was washed 5 times with a washing buffer (50 mM imidazole and protease inhibitor) and a Western blot experiment was performed to confirm the binding ability of the PROX1 neutralizing single chain antibody to the PROX1 protein (see FIG. 1).

Experimental Example 4. Verification of Neutralizing Efficacy of Humanized PROX1 Single-Chain Antibody 4.1. In Vitro Neutralization Efficacy Verification (In Vitro)

Figure 3A:
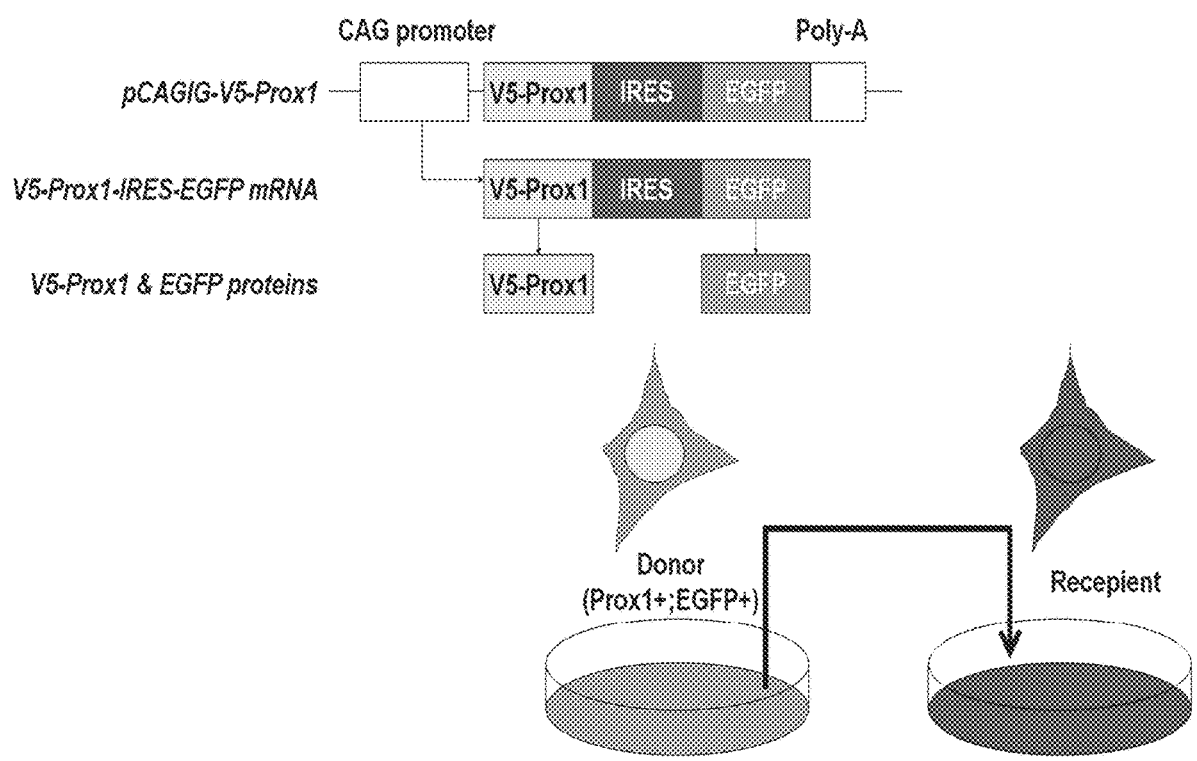
FIG. 3A is a diagram showing a method of confirming the neutralizing efficacy of a humanized PROX1 single chain antibody in vitro. 3B is a diagram in which the neutralizing efficacy of the humanized PROX1 single-chain antibody was confirmed through immunofluorescence staining.

The neutralizing efficacy of the humanized PROX1 single-chain antibody (anti-PROX1-scFv-hFc) was confirmed and verified by confirming the effect of inhibiting PROX1 protein migration between cultured cells (see FIGS. 3A and 3B).

As a result, when the culture medium of the control cell was treated (control media), the PROX1 protein (jade color) migrated from the donor cell (green cell, white arrow) to the recipient cell (red cell, yellow arrow) and was present in the recipient cell (yellow solid circle), but when the humanized PROX1 neutralizing single chain antibody was treated, it was confirmed that the PROX1 protein was not present in the recipient cell (yellow arrow) (white dotted circle) (see FIG. 3B).

This means that the humanized PROX1 single-chain antibody can effectively inhibit the intercellular migration of PROX1 protein, which means that this antibody has a neutralizing effect on PROX1 protein.

4.2. Verification of Neutralizing Efficacy In Vivo (In Vivo)

MNU was injected into the abdominal cavity of mice to damage the retina, and after 1 day, control growth medium (1 µl) or humanized PROX1 neutralizing single chain antibody (1 µl) was injected into the mouse eye. At this time, all injection solutions were loaded into a Hamilton syringe equipped with a Blunt 33-gauge needle and injected into the vitreal space of the mouse eye.

Figure 4B:
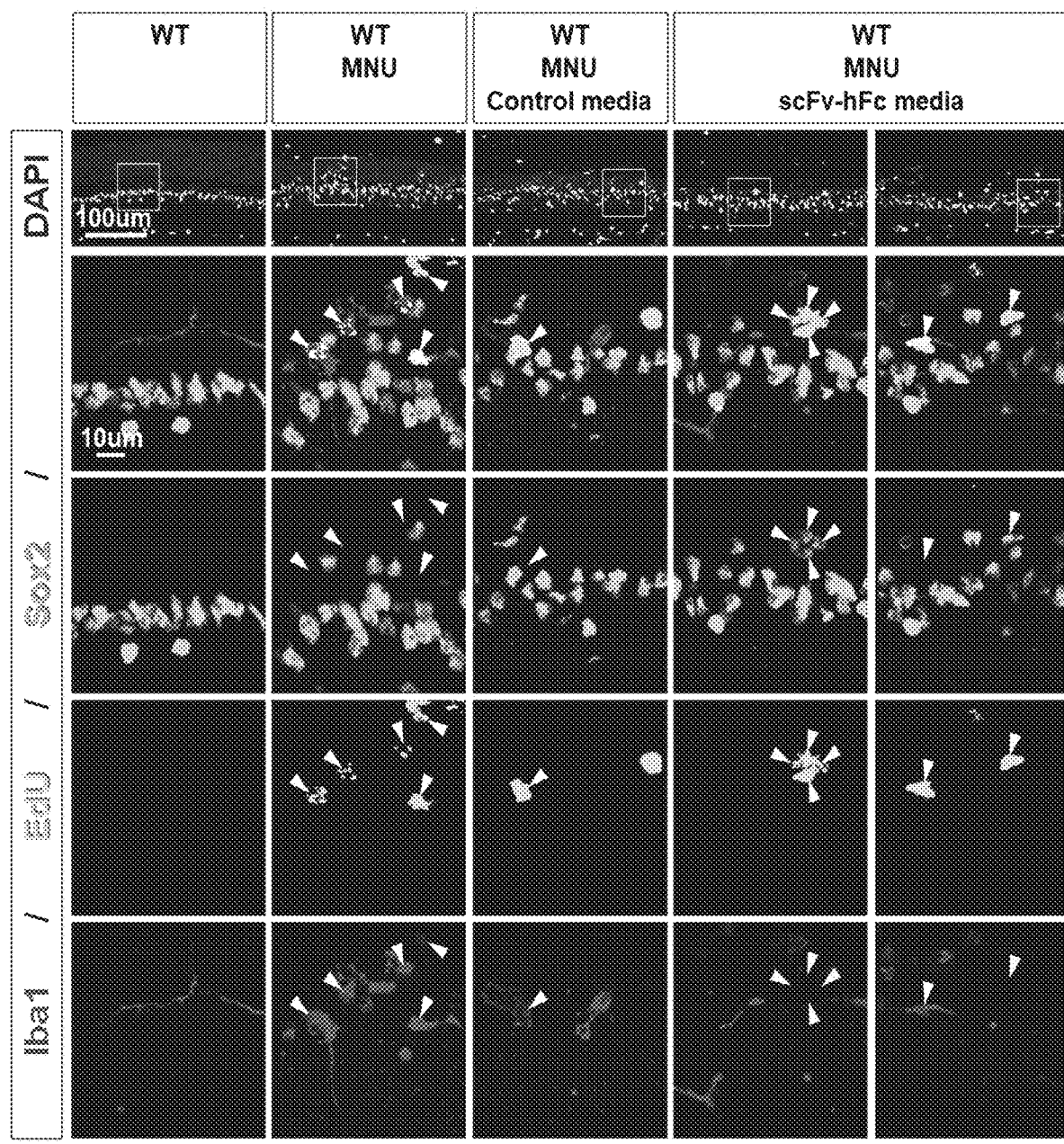
FIG. 4B is a diagram confirming the function of the humanized PROX1 single-chain antibody (anti-PROX1-scFv-hFc) promoting Müller glia cell division by inhibiting the migration of PROX1 protein by immunofluorescence staining.

Mouse eyeballs were harvested 3 days after intraocular injection, and the effect of inhibiting PROX1 protein migration and promoting cell division of humanized PROX1 single-chain antibodies in damaged mouse retinas was confirmed by immunofluorescence staining (IHC). At this time, the newly generated cells were labeled with EdU (see FIG. 4).

In damaged normal mouse retinas (second panel from left) and mouse retinas injected with control cell culture fluid (third panel from left), almost all neoplasms labeled with EdU, meaning cell division, turned out to be microglia inducing inflammatory responses labeled with IBA1 rather than Müller glia labeled with Sox2 (white arrow), while in mouse retinas injected with cell culture fluid containing humanized PROX1 single-chain antibodies (first and second panels from right), many of the new cells labeled with EdU turned out to be Müller glia labeled with Sox2 (yellow arrow).

These results suggest that the researcher's newly created humanized PROX1 single-chain antibody can effectively inhibit the migration of PROX1 protein from damaged mouse retinas to Müller glia, thereby inducing Müller glia cleavage.

Experimental Example 5. Mouse Intraocular AAV Injection

The second serotype adeno-associated virus (AAV2/2-IL2'SP-anti-PROX1-scFv-Flag) expressing the secretory PROX1 single-chain antibody was loaded into the eyes of mice 30 days after birth into a Hamilton syringe equipped with a Blunt 33-gauge needle in the same manner as above and injected (1 µl) and bred for an additional 20 days so that the antibody could be sufficiently expressed in the retina.

After 20 days, MNU reagent was injected into the abdominal cavity to induce retinal damage, and again after 4 days, mouse eyeballs were harvested to confirm the expression of IL2'SP-anti-PROX1-scFv-Flag in the damaged mouse retina.

Mouse eyes were isolated for subsequent fixation in PBS containing 4% paraformaldehyde (PFA) for 1 hour. Samples were then transferred to a 20% sucrose/PBS solution for subsequent culture at 4° C. for 16 hours prior to cryopreservation in Tissuetec O.C.T. Frozen mouse eye tissue sections (20 µm) were incubated in a blocking solution (PBS containing 10% donkey serum and 0.1% Triton X-100) for 1 hour at room temperature. Next, the tissue fragments were treated with a blocking solution containing a primary antibody without Triton X-100 added and incubated at 4° C. for 16 hours (Rb-anti-Prox1 (milipore), EdU-cy5 (invitrogen), Rabbit-anti-Iba1 (Wako), Goat-anti-Sox2 (R&D), mouse-anti-Flag (sigma)). The fluorophore-conjugated secondary antibody was then treated and cultured, and then the fluorescence signal of the tissue section was observed and analyzed with the Olympus FV1000 confocal microscope.

As a result, it was confirmed that PROX1 single-chain antibodies were very effectively and strongly expressed (jade color) in mouse retinas (first and second panels from right) injected with AAV2/2-IL2'SP-anti-PROX1-scFv-Flag (see FIG. 5B).

Figure 6:
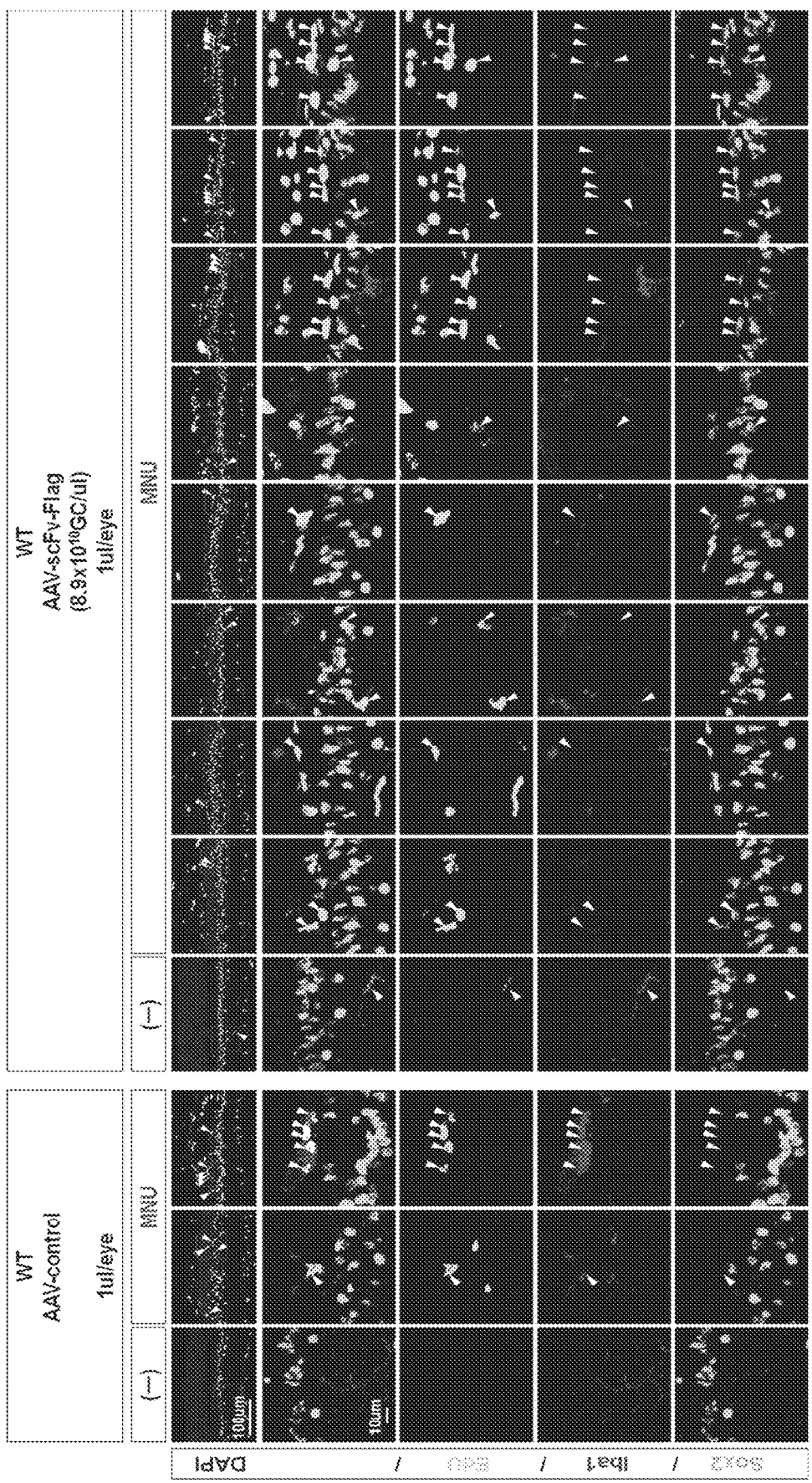
FIG. 6 is a diagram in which the function of promoting Müller glia cell division through inhibition of PROX1 protein migration in vivo of secretory PROX1 single-chain antibodies was confirmed through immunofluorescence staining.

Experimental Example 6. Confirmation of the Function of PROX1 Single-Chain Antibody to Promote Müller Glia Cell Division by Inhibiting PROX1 Protein Migration In Vivo In order to confirm the PROX1 protein migration inhibitory effect and cell division promotion effect of the PROX1 single-chain antibody, secretory PROX1 single-chain antibody-expressing adeno-attached virus (AAV2/2-IL2'SP-anti-PROX1-scFv-Flag) and a control group of adeno-attached virus were injected into the mouse eye as shown in FIG. 5A, and the Müller glia division in the mouse retina was irradiated by immunofluorescence staining (see FIG. 6).

In mouse retinas expressing control group of adeno-attached virus, almost all neoplasms labeled with EdU, meaning cell division, turned out to be microglia inducing inflammatory responses labeled with IBA1 rather than Müller glia labeled with Sox2 (white arrow), while in mouse retinas injected with secretory PROX1 single-chain antibody-expressing adeno-attached virus, many of the neoplasms labeled with EdU turned out to be Müller glia labeled with Sox2 (yellow arrow).

These results mean that the PROX1 neutralizing single chain antibody can effectively inhibit the migration of PROX1 protein from the damaged mouse retina to Müller glia, thereby inducing the division of Müller glia.

What is claimed is:

1. An antibody or binding fragment thereof that specifically binds to the PROX1 protein, wherein the antibody or binding fragment thereof comprises
    a) a light chain variable region comprising a CDR1 region comprising the amino acid sequence of SEQ ID NO: 6, a CDR2 region comprising the amino acid sequence of SEQ ID NO: 7, and a CDR3 region comprising the amino acid sequence of SEQ ID NO: 8; and
    b) a heavy chain variable region comprising a CDR1 region comprising the amino acid sequence of SEQ ID NO: 9, a CDR2 region comprising the amino acid sequence of SEQ ID NO: 10, and a CDR3 region comprising the amino acid sequence of SEQ ID NO: 11.

2. The antibody or binding fragment thereof according to claim 1, wherein the antibody or binding fragment thereof comprises
    a) a light chain variable region comprising the amino acid sequence of SEQ ID NO: 3; and
    b) a heavy chain variable region comprising the amino acid sequence of SEQ ID NO: 4.

3. The antibody or binding fragment thereof according to claim 1, wherein the antibody or binding fragment thereof is a scFv fragment, scFv-Fc fragment, Fab fragment, Fv fragment, diabody, chimeric antibody, or humanized antibody.

4. The antibody or binding fragment thereof according to claim 3, wherein the antibody is a humanized single chain antibody, an antibody or binding fragment thereof.

5. The antibody or binding fragment thereof according to claim 1, wherein the antibody or binding fragment thereof has the ability to neutralize PROX1 protein migration to any cell types.

* * * * *